US006482996B1

(12) United States Patent
Eichinger et al.

(10) Patent No.: US 6,482,996 B1
(45) Date of Patent: Nov. 19, 2002

(54) METHOD FOR THE PRODUCTION OR PREPARATION OF 2,6-DICHLOROTOLUOL

(75) Inventors: Wolfram Eichinger, Vaihingen (DE); Andreas Schulze-Tilling, League City, TX (US); Kai Röhlk, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/070,596

(22) PCT Filed: Aug. 28, 2000

(86) PCT No.: PCT/EP00/08364

§ 371 (c)(1),
(2), (4) Date: Apr. 12, 2002

(87) PCT Pub. No.: WO01/17932

PCT Pub. Date: Mar. 15, 2001

(30) Foreign Application Priority Data

Sep. 9, 1999 (DE) .......................................... 199 43 035

(51) Int. Cl.$^7$ .............................................. C07C 17/00
(52) U.S. Cl. ..................................................... 570/204
(58) Field of Search ......................................... 570/204

(56) References Cited

U.S. PATENT DOCUMENTS 4,749,817 A * 6/1988 George et al.

FOREIGN PATENT DOCUMENTS

| DE | 43 34 792 | 4/1995 |
|---|---|---|
| DE | 44 26 390 | 8/1995 |
| JP | 40-012694 | 6/1965 |

OTHER PUBLICATIONS

Catalytic Hydrogenation over Platinum Metals, Academic Press (month unavailable) 1967, pp. 405–425, Paul N. Rylander, "Catalytic Dehalogenation".

Heterogeneous Catalysis for the Synthetic Chemist, R. L. Augustine, Marcel Dekker Inc. (month unavailable) 1995, p. 534–537, C–X Bonds.

*Patent Abstracts of Japan, vol. 006, No. 007 (C–087) Jan. 16, 1982 & JP 56 133221 A (Hodogaya Chem Co Ltd), Oct. 19, 1981.

* cited by examiner

Primary Examiner—Alan Siegel
(74) Attorney, Agent, or Firm—Joseph C. Gil; Diderico van Eyl

(57) ABSTRACT

Disclosed is a method for the production or preparation of 2,6-dichlorotoluol by the catalytic hydrodechlorination of polychlorotoluol-containing mixtures in the presence of hydrogen, whereby the reaction is performed in the presence of an aluminium silicate-supported Pd-containing catalyst.

19 Claims, No Drawings

METHOD FOR THE PRODUCTION OR PREPARATION OF 2,6-DICHLOROTOLUOL

This application is the National Stage Application of PCT/EP00/08364, which claims a priority from German Application 199 43035.7, filed Sep. 9, 1999.

The present invention relates to a process for the preparation or isolation of 2,6-dichlorotoluene by catalytic hydrodechlorination of mixtures containing polychlorotoluenes.

2,6-Dichlorotoluene is an important intermediate for preparing various active compounds for agrochemicals and pharmaceuticals. The preparation of chlorotoluene usually results in the formation of isomeric mixtures of dichlorotoluenes and trichlorotoluenes from which, however, 2,6-dichlorotoluene has hitherto not been able to be selectively separated and which therefore have to be disposed of at high cost.

It is known in principle from "Catalytic Hydrogenation over Platinum Metals" (P. N. Rylander, Academic Press 1967, pages 405–425) that chlorobenzenes can be hydrodechlorinated in the presence of hydrogen over catalysts based on metals of the platinum group. However, owing to the usually only low selectivity, only partial conversions are generally achieved. It is also stated that reaction rate and conversion of hydrodehalogenations can be increased by the addition of bases such as sodium acetate or alkali metal hydroxide. On page 417 of "Catalytic Hydrogenation over Platinum Metals", it is indicated that halogen radicals can easily be removed from aromatic rings and that it is very difficult to retain a particular proportion of halogen radicals on the aromatic ring, which is why the formation of only cyclohexane is frequently observed. Activated carbon is reported as support material for the catalysts (see page 425). Furthermore, "Heterogeneous Catalysis for the Synthetic Chemist" (R. L. Augustine, Marcel Dekker Inc. 1995, p. 534–537) discloses that the use of nonpolar solvents such as ethyl acetate, benzene or cyclohexane leads to a reduction in the dechlorination rate. German Offenlegungsschrift 43 34 792 discloses a process for the hydrodehalogenation of halogenated benzenes in which use is made of catalysts obtained by application of one or more salts of Pd and/or Pt and, if desired, a copper salt to an aluminium oxide or titanium dioxide support material. The object of the process is the reconversion of more highly halogenated benzenes into the useful materials benzene and monochlorobenzene. In the description of this process, emphasis is given to the good conversions and the fact that the hydrodehalogenation of dihalogenobenzenes or trihalogenobenzenes forms virtually no cyclohexane or cyclohexane derivatives. The question of selectivity of the hydrodehalogenation is not accorded any importance because of the lack of other non-halogen substituents on the benzene ring.

JP 40-12694 B4 describes a process for the selective preparation of 2,6-dichlorotoluene by hydrodechlorination of 2,3,6-trichlorotoluene, in which a palladium-containing catalyst is used. As an essential condition for this process, it is emphasized that it is carried out in the liquid phase. It is also stated that the catalyst can contain any support material. Explicit mention is made of carbon, activated carbon, carbon black, barium sulphate, silica and diatomaceous earth as supports. In the examples, the palladium-on-activated carbon catalyst is introduced into the starting material mixture, the reaction temperature is set and hydrogen is blown through the resulting melt. The product mixture is subsequently discharged from the reactor in gaseous form together with an excess of hydrogen and is then condensed. Our own studies have shown that this process has the disadvantage that the palladium catalyst described in the examples loses its activity very quickly, i.e. has a short operating life, so that a change of catalyst is necessary at short intervals.

It is therefore an object of the present invention to provide a process which makes it possible to prepare or isolate 2,6-dichlorotoluene with high selectivity and to find a catalyst which at the same time has an improved long-term stability.

The invention provides a process for the preparation or isolation of 2,6-dichlorotoluene by catalytic hydrodechlorination of mixtures containing polychlorotoluenes in the presence of hydrogen, characterized in that the hydrodechlorination is carried out in the presence of a Pd-containing catalyst on an aluminium silicate support.

As mixtures containing polychlorotoluenes, preference is given to using mixtures containing dichlorotoluenes and/or trichlorotoluenes in the process of the invention. Surprisingly, this process makes it possible to hydrodechlorinate such isomer mixtures of various dichlorotoluenes and/or trichlorotoluenes over a long period of operation with excellent selectivity and to isolate 2,6-dichlorotoluene in high purity from the reaction product.

It has been found to be useful to employ dichlorotoluene mixtures containing at least 5% by weight, preferably at least 15% by weight and in particular at least 30% by weight, of 2,6-dichlorotoluene, based on the total dichlorotoluene mixture.

It has also been found useful to employ trichlorotoluene mixtures which contain at least 40% by weight, preferably at least 50% by weight and in particular at least 60% by weight, of 2,x,6-trichlorotoluenes, based on the total trichlorotoluene mixture, where x can represent 3, 4 and/or 5.

An essential aspect of the process of the invention is the use of supported Pd-containing catalysts in which the catalyst support contains an aluminium silicate. Such support materials are known to those skilled in the art. The term aluminium silicate is used as a generic term for compounds having various proportions of $Al_2O_3$ and $SiO_2$. Aluminium silicates include, for example, zeolites, feldspars and feldspar-like compounds. Aluminium silicates also include the trimorphic group $Al_2SiO_5$ ($Al_2O_3.SiO_2$). Aluminium silicates which do not crystallize well or amorphous aluminium silicates can also be used. Preference is given to using amorphous aluminosilicates and zeolites. The aluminium silicate support materials to be used according to the invention preferably have an $SiO_2:Al_2O_3$ weight ratio of (200–1):(1–200), particularly preferably (20–1):(1–20).

The finding made by the present invention that the use of a specific catalyst support is essential to the activity, selectivity and operating life of the catalyst in the preparation or isolation of 2,6-dichlorotoluene goes significantly beyond the teachings of JP 40-1294 B4, since that reference attaches no importance to the question as to whether the hydrodechlorination is improved at all by the use of a catalyst support and, if yes, by which catalyst support.

It has been found to be useful to employ support materials containing aluminium silicate and having a specific pore volume of greater than 10 ml/kg, preferably in the range 10–1000 ml/kg and in particular in the range 200–800 ml/kg. The BET surface area of the support materials is 5–800 $m^2/g$, preferably 10–500 $m^2/g$ and in particular 50–500 $m^2/g$.

The catalysts used contain, as catalytically active metal component, palladium in an amount of 0.1–10% by weight, preferably 0.5–5% by weight, based on the total catalyst. Apart from palladium, the catalysts can also contain further metals which promote the selective hydrodechlorination, e.g. copper in elemental and/or ionic form or else other metals of transition group VIII of the Periodic Table, e.g. ruthenium, rhodium or platinum. If copper is present as further component, the weight ratio of copper to palladium is preferably (0.5–50):100, in particular (1–10):100. If one or more metals of transition group VIII of the Periodic Table is/are present, the weight ratio of these metals to palladium is (0.02–0.5):1, preferably (0.05–0.2):1. Preference is given to using catalysts on aluminium silicate supports which have only palladium as catalytically active metal component.

It is possible to use either catalysts in which the metals are present only in an outer surface zone of the catalyst particle, known as coated catalysts, or catalysts in which the metals are distributed homogeneously through the catalyst particle.

To produce the catalysts, palladium in the form of its compounds such as ammonium hexachloropalladate, dihydrogen tetrachloropalladate, sodium tetrachloropalladate, potassium tetrachloropalladate, ammonium tetrachloropalladate, palladium nitrate, diamminedichloropalladium, diamminedinitropalladium, palladium oxide, bisacetylacetonatopalladium(II), palladium acetate, bis(dibenzylideneacetone)palladium(0), bis(acetonitrile)dichloropalladium(II), dichloro(cycloocta-1,5-diene)palladium(II) or allyl(pentadienyl)-palladium(II) or in colloidal form is fixed to the support material containing aluminium silicate. If copper is present as active metallic catalyst component in the catalysts, this is likewise fixed in the form of its compounds such as copper chloride, copper nitrate, copper oxide, copper sulphate, copper citrate, copper oxalate or copper acetate or in colloidal form to the support material containing aluminium silicate. The application of one or more other metals of transition group VIII of the Periodic Table, e.g. ruthenium, rhodium or platinum, is analogous.

The application of the metal components to the support can be carried out by methods known to those skilled in the art. For example, the aluminium silicate catalyst support can be impregnated with a solution of the metal component(s), preferably in water. The amount of solution is preferably such that the volume of the impregnation solution corresponds to the pore volume of the support. To apply relatively large amounts of the metal component(s), the impregnation can be repeated a number of times. It is also possible for the support material and the metal component(s) to be mixed with a liquid. The metal component(s) is/are preferably used in dissolved form. If desired, a precipitation reagent or a reducing agent is added to the mixture in order to deposit all of the metal component(s) on the support. The liquid can subsequently be removed, e.g. by filtration or distillation. It is also possible to spray the support with a solution of the metal compound(s) in a heated rotating drum and to evaporate the water at the same time.

The aluminium silicate support material can be used in powder form or as shaped bodies such as granules, extrudates or as tablets. If pulverulent support materials are used, shaped catalyst bodies can likewise be produced therefrom after application of the metal components, e.g. by extrusion or tableting.

If the catalysts are used in powder form in the process of the invention, it has been found to be useful to carry out the reaction in suspension reactors such as stirred vessels or bubble column reactors. When using the catalyst in particulate form, on the other hand, fixed-bed reactors are preferred. It is particularly preferred to fix the catalyst as a fixed bed in a tube reactor. The hydrogen-containing reaction mixture is then passed through the tube reactor in the form of a hydraulic liquid, a trickle phase or a shower phase.

The catalyst obtained after application of the metal components to the support material can be used immediately in the process of the invention or else can be dried, calcined and/or activated using reducing agents, e.g. hydrogen, before use. This activation is carried out at a temperature of 50–250° C., preferably 100–200° C. and particularly preferably 130–180° C., and a hydrogen pressure of 0.1–10 bar, preferably 0.5–5 bar and in particular 1–4 bar.

The process of the invention itself is carried out at 100–250° C., preferably 130–240° C. and in particular 150–230° C.

Hydrogen can be used in the process of the invention in customary grades. It has been found to be useful to work at a total pressure of 1–20 bar, preferably 1–10 bar and in particular 1–6 bar. The hydrogen can also be used in admixture with an inert gas, e.g. nitrogen, argon, helium or methane. The hydrogen content of such mixtures can be, for example, 10–90% by volume.

The process of the invention can be carried out continuously or batchwise, preferably continuously.

In the continuous procedure, the WHSV (weight hourly space velocity: mass flow of starting material per unit catalyst mass and unit time), is 0.05–1/h, preferably 0.1–0.5/h and in particular 0.1–0.3/h.

The hydrogen flow used is usually 1–100 standard l/(kg of catalyst and hour), preferably 10–90 standard l/(kg of catalyst and hour) and in particular 25–75 standard l/(kg of catalyst and hour).

When the process of the invention is carried out continuously, the usual procedure is to pump the polychlorotoluene-containing mixtures used together with the hydrogen as a liquid or liquid/gas phase through a reactor containing the catalyst at the desired reaction temperature.

The hydrodechlorination of the invention leads to reaction mixtures in which the desired 2,6-dichlorotoluene is present in a good yield and can easily be separated off in high purity by distillation and crystallization. 2,5-Dichlorotoluene, which cannot be separated from 2,6-dichlorotoluene at all by distillation and is therefore theoretically a critical impurity in 2,6-dichlorotoluene, is present in only an extremely small amount in the reaction mixtures. Furthermore, the process of the invention displays a very high catalyst operating life and excellent catalyst reusability.

An advantage of the process of the invention is that the catalyst can easily be separated from the reaction mixture by industrial separation operations and can be reused without a loss of activity.

The process of the invention not only makes it possible to obtain 2,6-dichlorotoluene simply and selectively by hydrodechlorination of mixtures of polychlorinated toluenes but also makes it possible to recover monochlorotoluenes, in particular 2-chlorotoluene. These substances are valuable raw materials which can thus be returned to the raw materials cycle.

If dichlorotoluene isomer mixtures are used as starting materials, the process of the invention results in selective hydrodechlorination of 2,4- and 2,5-dichlorotoluene, while, in contrast, 2,6-dichlorotoluene is hydrodechlorinated to only a slight extent. At the same time, little toluene is formed. This is particularly advantageous because toluene would have to be chlorinated again in order to be brought back into the cycle of desired materials.

If trichlorotoluene isomer mixtures are used as starting materials, 2,6-dichlorotoluene is preferentially formed in the hydrodechlorination.

EXAMPLES

I Catalyst Production

Example A 84 g of amorphous aluminosilicate (bulk density: 840 g/l, mean particle size: 1–3 mm; specific surface area: 420 m²/g; silicon dioxide content: 77% by weight; aluminium oxide content: 10% by weight) are impregnated with 22.7 ml of an aqueous solution of 16 g of sodium tetrachloropailadate and dried in air at 110° C. for 4 hours.

Example B

Using a method analogous to Example 1, a catalyst is produced using the following support material.

Amorphous aluminosilicate (bulk density: 370 g/l; mean particle size: 1.7 mm; pore volume: 600 ml/g; specific surface area: 305 m²/g, silicon dioxide content: 40% by weight; aluminium oxide content: 60% by weight)

Example C 25 g of zeolite H-ZSM 5 are impregnated with 9 ml of an aqueous solution of 0.125 g of diamminedichloropalladium, allowed to stand for 24 hours and dried in air at 110° C. for 4 hours.

II Hydrodechlorination

Experiment 1

100 g of the catalyst produced in Example A are placed in a reactor tube having an internal diameter of 1.8 cm (bed height: 42 cm). The reactor tube is subsequently heated to 175° C. and hydrogen is passed through it.

After one hour under these reaction conditions, a volume flow of 10 ml/h of a mixture consisting of

| | |
|---|---|
| 23.4% | of 2,4-dichlorotoluene |
| 40.4% | of 2,5-dichlorotoluene and |
| 36.2% | of 2,6-dichlorotoluene | is pumped together with 5 standard l/h of hydrogen through the reactor at a temperature of 170° C. and a pressure of 1–3 bar. The product mixture is cooled to room temperature after leaving the reactor and the phases are separated. The composition of the liquid crude product phase determined by GC analysis is reported in the table below.

The same composition of the product mixture is also obtained after a reaction time of 1000 hours, which demonstrates the high stability of the catalyst.

Comparative Example 1

Pd on Activated Carbon

The procedure of Experiment 1 is repeated using a Pd catalyst in which 10% of Pd has been applied to activated carbon as support material. At a reaction temperature of 160° C. and a hydrogen flow of 2.6 standard l/h, the product mixture obtained after 60 hours has the composition reported in the table below.

After an operating time of only 160 hours, the catalyst displays only a minimal remaining hydrodechlorination activity.

Comparative Example 2

Pd on SiO₂

This comparative example is carried out using a method analogous to Experiment 1, but using SiO₂ as support material. The composition of the product mixture obtained is reported in the table below.

Even at lower reaction temperatures (110–150° C.), this catalyst converts the dichlorotoluene mixture unselectively into a methylcyclohexane/toluene mixture, with the toluene content rising with increasing temperature.

Comparative Examples 3 a–c

Pd on Al₂O₃

This comparative experiment is likewise carried out using a method analogous to Experiment 1, but using Al₂O₃ as support material. The product mixture compositions obtained at various reaction temperatures are reported in the table below.

The table also shows the ratio of 2,5-dichlorotoluene:2, 6-dichlorotoluene, since 2,5-dichlorotoluene cannot be separated from 2,6-dichlorotoluene and is thus present as an impurity in the 2,6-dichlorotoluene even after purification of the crude product mixtures indicated below.

| | Experiment | Comparative experiments | | | | |
|---|---|---|---|---|---|---|
| | 1 | 1 | 2 | 3a | 3b | 3c |
| Support material | Al₂O₃/SiO₂ | Activated carbon | SiO₂ | Al₂O₃ | Al₂O₃ | Al₂O₃ |
| Reaction temperature [° C.] | 170 | 160 | 170 | 170 | 150 | 130 |
| Hydrogen [standard l/h] | 5 | 2,6 | 5 | 5 | 5 | 5 |
| Composition [% by weight] | | | | | | |
| Methylcyclohexane | — | — | 18 | 2 | 3.3 | 4.5 |
| Toluene | 15 | 0.72 | 80 | 90 | 67 | 21 |
| 2-Chlorotoluene | 50 | 20.6 | 1 | 8 | 23.3 | 17.6 |
| 3-Chlorotoluene | 0.2 | — | — | — | — | — |
| 4-Chlorotoluene | 0.1 | — | — | — | — | — |
| 2,4-Dichlorotoluene | 1.9 | 19.1 | — | — | — | 11.0 |
| 2,5-Dichlorotoluene | 4.2 | 30.0 | — | — | 0.17 | 18.8 |
| 2,6-Dichlorotoluene | 27 | 26.9 | 0.17 | — | 5.7 | 26.0 |
| Ratio of 2,6-dichlorotoluene:2,5-dichlorotoluene | 6.4 | 0.9 | n.d. | — | 38.8 | 1.1 |

Experiment 2

Experiment 2 is carried out using a method analogous to Experiment 1. However, a mixture of

| | |
|---|---|
| 95% | of 2,3,6-trichlorotoluene |
| 1.8% | of 2,4,6-trichlorotoluene and |
| 1.8% | of 2,4,5-trichlorotoluene | in an amount of 10 ml/h and a hydrogen flow of 5 standard l/h are passed through the reactor tube at 200° C. Phase separation gives a product mixture having the composition reported in the table below.

The selectivity achieved is 45%.

|  | Experiment 2 |
| --- | --- |
| Methylcyclohexane | — |
| Toluene | 3.9 |
| 2-Chlorotoluene | 7.4 |
| 3-Chlorotoluene | — |
| 4-Chlorotoluene | — |
| 2,3-Dichlorotoluene | 9.6 |
| 2,4-Dichlorotoluene | 0.1 |
| 2,5-Dichlorotoluene | 0.4 |
| 2,6-Dichlorotoluene | 18.5 |
| 2,3,6-Trichlorotoluene | 57.3 |
| 2,4,6-Trichlorotoluene | 0.6 |
| 2,4,5-Trichlorotoluene | 1.1 |
| Ratio of 2,6-dichlorotoluene: 2,5-dichlorotoluene | 46.3 |

What is claimed is:

1. A process for preparing or isolating 2,6-dichlorotoluene comprising catalytically hydrodechlorinating a mixture containing polychlorotoluenes in the presence of (i) hydrogen and (ii) a palladium-containing catalyst on an aluminium silicate support.

2. The process according to claim 1, wherein the mixture containing polychlorotoluenes is a mixture selected from the group consisting of dichlorotoluenes, trichlorotoluenes, and mixtures thereof.

3. The process according to claim 2, wherein the mixture containing dichlorotoluenes contains at least 5% by weight of 2,6-dichlorotoluene, based on the dichlorotoluene mixture.

4. The process according to claim 3, wherein the dichlorotoluene fixture contains at least 15% by weight of 2,6-dichlorotoluene, based on the dichlorotoluene mixture.

5. The process according to claim 4, wherein the mixture containing dichlorotoluene contains at least 30% by weight of 2,6-dichlorotoluene, based on the dichlorotoluene mixture.

6. The process according to claim 2, wherein the mixture containing trichlorotoluenes contains at least 40% by weight, of 2,x,6-trichlorotoluenes, based on the trichlorotoluene mixture, wherein x represents 3, 4 and/or 5.

7. The process according to claim 2, wherein the mixture containing trichlorotoluenes contains at least 50% by weight of 2,x,6-trichlorotoluenes, based on the trichlorotoluene mixture, wherein x represents 3, 4 and/or 5.

8. The process according to claim 1, wherein the mixture containing trichlorotoluenes contains at least 60% by weight, of 2,x,6-trichlorotoluenes, based on the trichlorotoluene mixture, wherein x represents 3, 4 and/or 5.

9. The process according to claim 1, wherein the aluminium silicate catalyst support is a zeolite or an amorphous aluminosilicate.

10. The process according to claim 1, wherein the aluminium silicate catalyst support has an $SiO_2:Al_2O_3$ weight ratio of (200–1):(1–200).

11. The process according to claim 1, wherein the aluminium silicate catalyst support has an $SiO_2:Al_2O_3$ weight ratio of (20–1):(1–20).

12. The process according to claim 1, wherein the aluminium silicate support has a specific pore volume that is greater than 10 ml/kg, and a BET surface area ranging from 5 to 800 $m^2/g$.

13. The process according to claim 1, wherein the palladium-containing catalyst contains palladium in an amount ranging from 0.1 to 10% by weight, based on the catalyst.

14. The process according to claim 1, wherein the palladium-containing catalyst contains palladium in an amount ranging from from 0.5 to 5% by weight, based on the catalyst.

15. The process according to claim 1, wherein the palladium-containing catalyst further comprises a catalytically active metallic component selected from the group consisting of copper, a metal of transition group VIII of the Periodic Table, and mixtures thereof.

16. The process according to claim 1, wherein the palladium-containing catalyst further comprises a catalytically active metallic component selected from the group consisting of copper, a metal of transition group VIII of the Periodic Table, and mixtures thereof.

17. The process according to claim 1, wherein the palladium-containing catalyst further comprises a catalytically active metallic component selected from the group consisting of copper, rruthenium, rhodium, platinum, and mixtures thereof.

18. The process according to claim 1, wherein the process is carried out continuously or batchwise.

19. The process according to claim 1, wherein the process is carried out continuously.

\* \* \* \* \*